US009770707B2

(12) United States Patent
Joshi et al.

(10) Patent No.: US 9,770,707 B2
(45) Date of Patent: Sep. 26, 2017

(54) HETEROGENEOUS CATALYST FOR TRANSESTERIFICATION AND METHOD OF PREPARING SAME

(71) Applicant: Crystaphase Products, Inc., Houston, TX (US)

(72) Inventors: Umakant Pravinchandra Joshi, Houston, TX (US); Peter Gregory Ham, Houston, TX (US)

(73) Assignee: CRYSTAPHASE PRODUCTS, INC., Houston, TX (US)

( * ) Notice: Subject to any disclaimer, the term of this patent is extended or adjusted under 35 U.S.C. 154(b) by 0 days.

(21) Appl. No.: 15/341,736

(22) Filed: Nov. 2, 2016

(65) Prior Publication Data

US 2017/0043326 A1 Feb. 16, 2017

Related U.S. Application Data

(62) Division of application No. 14/753,623, filed on Jun. 29, 2015, now Pat. No. 9,643,163.

(Continued)

(51) Int. Cl.
*B01J 27/18* (2006.01)
*B01J 35/10* (2006.01)
(Continued)

(52) U.S. Cl.
CPC ......... *B01J 27/1806* (2013.01); *B01J 21/066* (2013.01); *B01J 23/04* (2013.01); *B01J 27/18* (2013.01); *B01J 35/0006* (2013.01); *B01J 35/1014* (2013.01); *B01J 35/1057* (2013.01); *B01J 35/1061* (2013.01); *B01J 37/031* (2013.01); *B01J 37/035* (2013.01);
(Continued)

(58) Field of Classification Search
None
See application file for complete search history.

(56) References Cited

U.S. PATENT DOCUMENTS

| 2,084,511 | A | | 6/1937 | Small | |
|---|---|---|---|---|---|
| 3,149,081 | A | * | 9/1964 | Bowman | B01J 27/18 502/208 |

(Continued)

FOREIGN PATENT DOCUMENTS

| WO | 2010113011 | 10/2010 |
|---|---|---|
| WO | 2016057913 | 4/2016 |
| WO | 2016168697 | 10/2016 |

OTHER PUBLICATIONS

European Patent Office; PCT International Search Report, Issued in connection to PCT/US2016/027892; Jul. 15, 2015; 4 pages; Europe.

(Continued)

*Primary Examiner* — Yate K Cutliff
(74) *Attorney, Agent, or Firm* — Greenberg Traurig LLP

(57) ABSTRACT

A transesterification catalyst that is heterogeneous and a method for preparing said transesterification catalyst are provided. The catalyst can be used in a variety of transesterification reactor configurations including CSTR (continuous stirred tank reactors), ebullated (or ebullating) beds or any other fluidized bed reactors, and PFR (plug flow, fixed bed reactors). The catalyst can be used for manufacturing commercial grade biodiesel, biolubricants and glycerin.

2 Claims, 6 Drawing Sheets

Related U.S. Application Data

(60) Provisional application No. 62/062,567, filed on Oct. 10, 2014, provisional application No. 62/149,138, filed on Apr. 17, 2015, provisional application No. 62/155,970, filed on May 1, 2015.

(51) Int. Cl.

| | | |
|---|---|---|
| *B01J 37/03* | (2006.01) | |
| *B01J 37/04* | (2006.01) | |
| *B01J 37/08* | (2006.01) | |
| *C07C 67/03* | (2006.01) | |
| *C07C 67/48* | (2006.01) | |
| *C07C 67/54* | (2006.01) | |
| *C10L 1/02* | (2006.01) | |
| *B01J 21/06* | (2006.01) | |
| *B01J 23/04* | (2006.01) | |
| *B01J 35/00* | (2006.01) | |
| *C01B 25/45* | (2006.01) | |

(52) U.S. Cl.
CPC ........... *B01J 37/036* (2013.01); *B01J 37/038* (2013.01); *B01J 37/04* (2013.01); *B01J 37/08* (2013.01); *C01B 25/45* (2013.01); *C07C 67/03* (2013.01); *C07C 67/48* (2013.01); *C07C 67/54* (2013.01); *C10L 1/026* (2013.01); *Y02E 50/13* (2013.01); *Y02P 20/582* (2015.11)

(56) References Cited

U.S. PATENT DOCUMENTS

| | | | |
|---|---|---|---|
| 5,162,589 | A | 11/1992 | Wijngaarden et al. |
| 7,741,502 | B2 | 6/2010 | Lecocq et al. |
| 7,754,643 | B2 | 7/2010 | Srinivas et al. |
| 7,795,460 | B2 | 9/2010 | Elliott |
| 7,842,653 | B2 | 11/2010 | Darbha et al. |
| 8,124,801 | B2 | 2/2012 | Srinivas et al. |
| 8,962,873 | B2 | 2/2015 | Summers et al. |
| 9,085,547 | B2 | 7/2015 | Jonsson et al. |
| 9,643,163 | B2 | 5/2017 | Joshi et al. |
| 2002/0010359 | A1 | 1/2002 | Kaita et al. |
| 2008/0257781 | A1 | 10/2008 | Lecocq et al. |
| 2009/0145022 | A1 | 6/2009 | Ng et al. |
| 2010/0170143 | A1 | 7/2010 | McNeff et al. |
| 2011/0185625 | A1 | 8/2011 | Singh et al. |
| 2011/0245527 | A1 | 10/2011 | Ooms et al. |
| 2012/0029218 | A1 | 2/2012 | Kim et al. |
| 2012/0130101 | A1 | 5/2012 | Yoo et al. |
| 2012/0240452 | A1 | 9/2012 | Erdoes, Jr. et al. |
| 2013/0164798 | A1 | 6/2013 | Vanhercke et al. |
| 2014/0046104 | A1 | 2/2014 | McNeff et al. |
| 2014/0109466 | A1 | 4/2014 | Schmidt et al. |
| 2014/0206833 | A1 | 7/2014 | Fernandez et al. |
| 2014/0296583 | A1 | 10/2014 | Frey et al. |
| 2016/0102041 | A1 | 4/2016 | Joshi et al. |
| 2016/0303545 | A1 | 10/2016 | Joshi et al. |
| 2017/0043326 | A1 | 2/2017 | Joshi et al. |

OTHER PUBLICATIONS

European Patent Office; PCT Written Opinion of the International Searching Authority, Issued in connection to PCT/US2016/027892; Jul. 15, 2015; 8 pages; Europe.

European Patent Office; PCT International Search Report, Issued in connection to PCT/US2015/054930; Feb. 2, 2016; 4 pages; Europe.

European Patent Office; PCT Written Opinion of the International Searching Authority, Issued in connection to PCT/US2015/054930; Feb. 2, 2016; 7 pages; Europe.

Kumar et al.; Phase Assemblage Stucy and Cytocompatibility Property of Heat Treated Potassium Magnesium Phosphate-Silicate Ceramics; 2009; Journal of Mater Sci.; Mater Med. 20; pp. 1689-1695.

Skogareva et al.; Nanostructured Sodium Calcium Tripolyphosphate and its Peroxo Derivatives are a New Generation of Bioceramic Materials; 2011; Russian Journal of Inorganic Chemistry, vol. 56, No. 7; pp. 1004-1011.

I.K. Lloyd et al.; "Sintering and Characterization of Alkaline-Earth-Doped and Zirconium-Dificient Na3Zr2Si2P012;" Solid State Ionics; vol. 11, No. 1; Sep. 1, 1993; 6 pages; North Holland Publishing Company; Amsterdam, NL.

Yue Y et al.; "Hydrothermal Crystallization and Structural Investigation of Na1+2xZr2-xMgx(P04)3 Systems;" Materials Chemistry and Physics; vol. 35, No. 1; Aug. 1, 1993.

Wen Cheng Chen et al.; "Green Synthesis of Calcium and Phosphate Compounds by Varying pH Value and Ca/P Atomic Ratio Using Aqueous Precipitations," Ceramics-Silikaty; Mar. 1, 2013; pp. 14-21; http://www.ceramics-silikaty.cz/2013/pdf/2013_01_014.pdf.

Kouzu et al.; Calcium Oxide as a Solid Base Catalyst for Transesterification of Soybean Oil and its Application to Biodiesel Production; Mar. 6, 2007; 9 pages; Elsevier.

European Patent Office; PCT International Search Report, Issued in connection to PCT/US2017/026772; dated Jul. 28, 2017; 5 pages; Europe.

European Patent Office; PCT Written Opinion of the International Searching Authority, Issued in connection to PCT/US2017/026772; dated Jul. 28, 2017; 10 pages; Europe.

\* cited by examiner

Overall Transesterification chemical reaction

HETEROGENEOUS CATALYST FOR TRANSESTERIFICATION AND METHOD OF PREPARING SAME

BACKGROUND

1. Related Applications

This application is a divisional application and claims the benefit, and priority benefit, of U.S. Non-Provisional patent application Ser. No. 14/753,623, filed Jun. 29, 2015, which claims the benefit, and priority benefit, of U.S. Provisional Patent Application Ser. No. 62/062,567, filed Oct. 10, 2014, U.S. Provisional Patent Application Ser. No. 62/149,138, filed Apr. 17, 2015 and U.S. Provisional Patent Application Ser. No. 62/155,970, filed May 1, 2015, the contents of each of which are incorporated by reference herein in their entirety.

2. Field of the Invention

The presently disclosed subject matter relates to a heterogeneous catalyst and use of the heterogeneous catalyst for transesterification.

3. Description of the Related Art

Transesterification is the reversible chemical reaction process of exchanging the organic group of an ester with the organic group of an alcohol. Transesterification processes became commercially popular in the 1940s as researchers explored ways to more readily produce glycerol (also called glycerin, glycerine and propanetriol) used in explosives manufacture during World War II. Currently, transesterification is an important step in industrial processes such as production of: acrylates from methymethacrylate, polyethylene terephthalate (PET) polymer manufacturing from ethylene glycol and either dimethyl terephthalate or terephthalic acid, and alkyl esters. Of particular current commercial interest is the transesterification of alcohol with triglyceride esters contained in oils and fats (primarily vegetable oils and animal fats) to form fatty acid alkyl esters and glycerin. These esters find commercial use as biodiesel fuel and biolubricants.

Catalysts known to facilitate the transesterification reaction include mineral acids and bases, metal alkoxides, nonionic bases and lipase enzymes. These catalysts include homogeneous species which are soluble in reactants and/or products and heterogeneous species which are solids and insoluble in reactants or products.

Alkaline metal alkoxides (e.g., $CH_3ONa$ for methanolysis) and alkaline metal hydroxides (NaOH and KOH) are catalysts for the homogeneous transesterification reaction. These catalysts are soluble in reactants and products and thus require extensive post-reaction treatment including product neutralization, salt removal and water wash to produce commercially acceptable products. These are non-trivial processes and costly to install, maintain and operate. Homogeneous enzymatic transesterification using lipase has been utilized for conversion of triglycerides to biodiesel, since the byproduct glycerin can be purified by flashing off the excess alcohol from the products. However, processing time can be lengthy for acceptable conversion of triglycerides and product clean-up costs are high to make commercial grade products.

Replacement of the homogeneous catalyst with heterogeneous catalyst has been commercialized notably with the Esterfip-H® process licensed by Axens and the ENSEL® process licensed by Benefuel. These heterogeneous catalyst processes can reduce post-reaction processing, but require reaction operating temperatures of 150 degrees C. to 250 degrees C. and alcohol partial pressure as high as 300 to 400 psi for the manufacture of biodiesel alkyl esters. These heterogeneous catalyst reactions must be carried out in fixed bed reactors due to the severity of the process conditions.

Improvements in this field of technology are desired to reduce the operating severity and costs of the transesterification reaction regime as well as the subsequent process clean-up and product purification steps. Improvements are also desired which allow use of new technology in existing or readily modified commercial facilities.

SUMMARY

According to the various illustrative embodiments disclosed herein, a transesterification catalyst that is heterogeneous and a method for preparing said transesterification catalyst are provided. For the purposes of this disclosure, the transesterification catalysts of the various illustrative embodiments will hereinafter be referred to as UMAKAT. Various means for transesterification using UMAKAT are also provided.

In certain illustrative embodiments, UMAKAT can be used in a variety of transesterification reactor configurations including CSTR (continuous stirred tank reactors), ebullated (or ebullating) beds or any other fluidized bed reactors, and PFR (plug flow, fixed bed reactors). UMAKAT can be used for manufacturing commercial grade biodiesel, biolubricants and glycerin.

In certain illustrative embodiments, a compound is provided. The compound can have the formula $Z_xQ_yPO_nMH_2O$, wherein Z is selected from the group consisting of potassium, sodium and lithium, Q is selected from the group consisting of calcium, magnesium and barium, x is a rational number in the range from 0.5 to 4, y is a rational integer in the range from 2 to 8, n is a rational integer in the range from 4 to 8, and M is a ceramic substrate, and wherein the compound is a transesterification catalyst. The total surface area of the compound can be greater than 20 square meters per gram. The active surface area of the compound can be greater than 20 square meters per gram. The average diameter of the pores in the compound can be in the range from 1-10 nanometers. The compound can be active at a temperature in the range from 40 to 70 degrees C. The compound can also be active at a temperature in the range from 40 to 130 degrees C.

In certain illustrative embodiments, a method of preparing a transesterification catalyst is provided. A metal hydroxide with the metal selected from the group consisting of potassium, sodium and lithium can be mixed with a metal hydroxide with the metal selected from the group consisting of calcium, magnesium, barium and lithium. The components can be mixed in a ratio of approximately 1:10 by weight to form a component mixture, in certain illustrative embodiments. The component mixture can be dissolved in phosphoric acid and heated to a temperature in the range from 60-90 degrees C. A solid compound can be precipitated and washed. The precipitate can be mixed with ceramic substrate powder in a ratio of approximately 2:10 by weight and washed with water. The precipitate/ceramic substrate mixture can be calcined. Calcination can occur at a temperature in the range from 400-500 degrees C. for 4 hours or greater.

In certain illustrative embodiments, a method of preparing an alkyl ester using a transesterification catalyst is provided. The alkyl ester can be suitable for use as biodiesel fuel, as a biodiesel additive to conventional diesel fuel, or as a biolubricant additive to conventional lubricants. The alkyl ester can also be suitable for use as a biolubricant. A transesterification catalyst can be provided. The catalyst can have the formula $Z_xQ_yPO_nMH_2O$, wherein Z is selected from the group consisting of potassium, sodium and lithium, Q is selected from the group consisting of calcium, magnesium and barium, x is a rational number in the range from 0.5 to 4, y is a rational integer in the range from 2 to 8, n is a rational integer in the range from 4 to 8, and M is a ceramic substrate. Triglycerides and alcohol can be reacted in the presence of said catalyst to convert the triglycerides and alcohol to alkyl ester and glycerin. The triglycerides can be triglyceride-containing fats and/or oils. The conversion can be essentially complete conversion of triglycerides. The glycerin can be separated from the reaction mixture. The reaction mixture can be filtered to recover the catalyst. The unreacted alcohol can be distilled from the alkyl ester and the glycerin. The method can be at least partially performed in a continuous stirred tank reactor. The method can also be at least partially performed in a fixed bed reactor. The method can also be at least partially performed in a fluidized bed reactor. The alkyl ester is capable of being used as biodiesel fuel, a biodiesel additive to conventional diesel fuel, a biolubricant additive to other lubricants or as a biolubricant.

While certain preferred illustrative embodiments will be described herein, it will be understood that this description is not intended to limit the subject matter to those embodiments. On the contrary, it is intended to cover all alternatives, modifications, and equivalents, as may be included within the spirit and scope of the subject matter as defined by the appended claims.

DETAILED DESCRIPTION

According to the various illustrative embodiments provided herein, UMAKAT is a solid, heterogeneous compound having the general formula $Z_xQ_yPO_nMH_2O$, where Z is selected from Group 1 metals including potassium, sodium and lithium, Q is selected from Group 2 metals including calcium, magnesium and barium, x is a rational number in the range from 0.5 to 4, y is a rational integer in the range from 2 to 8, and n is a rational integer in the range from 4 to 8. M can be any ceramic substrate such as, for example, zirconia, silica, alumina, or combinations thereof. The Group 1 and Group 2 alkali metals form a double metal salt catalyst, the phosphate ($PO_n$) makes it insoluble and the ceramic provides the solid support, in certain illustrative embodiments.

Figure 1A:
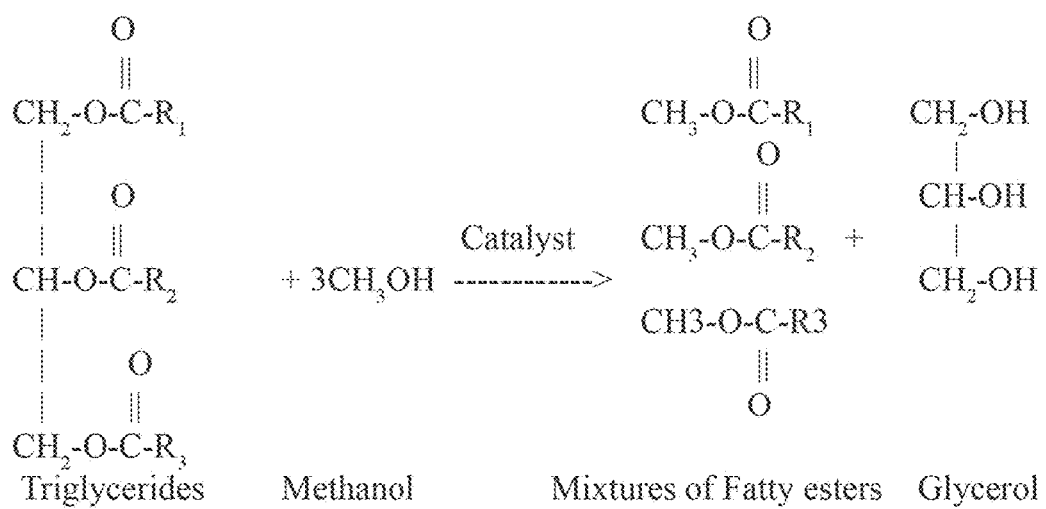
FIGS. 1A and 1B show an illustrative embodiment of a transesterification reaction.
Figure 1B:
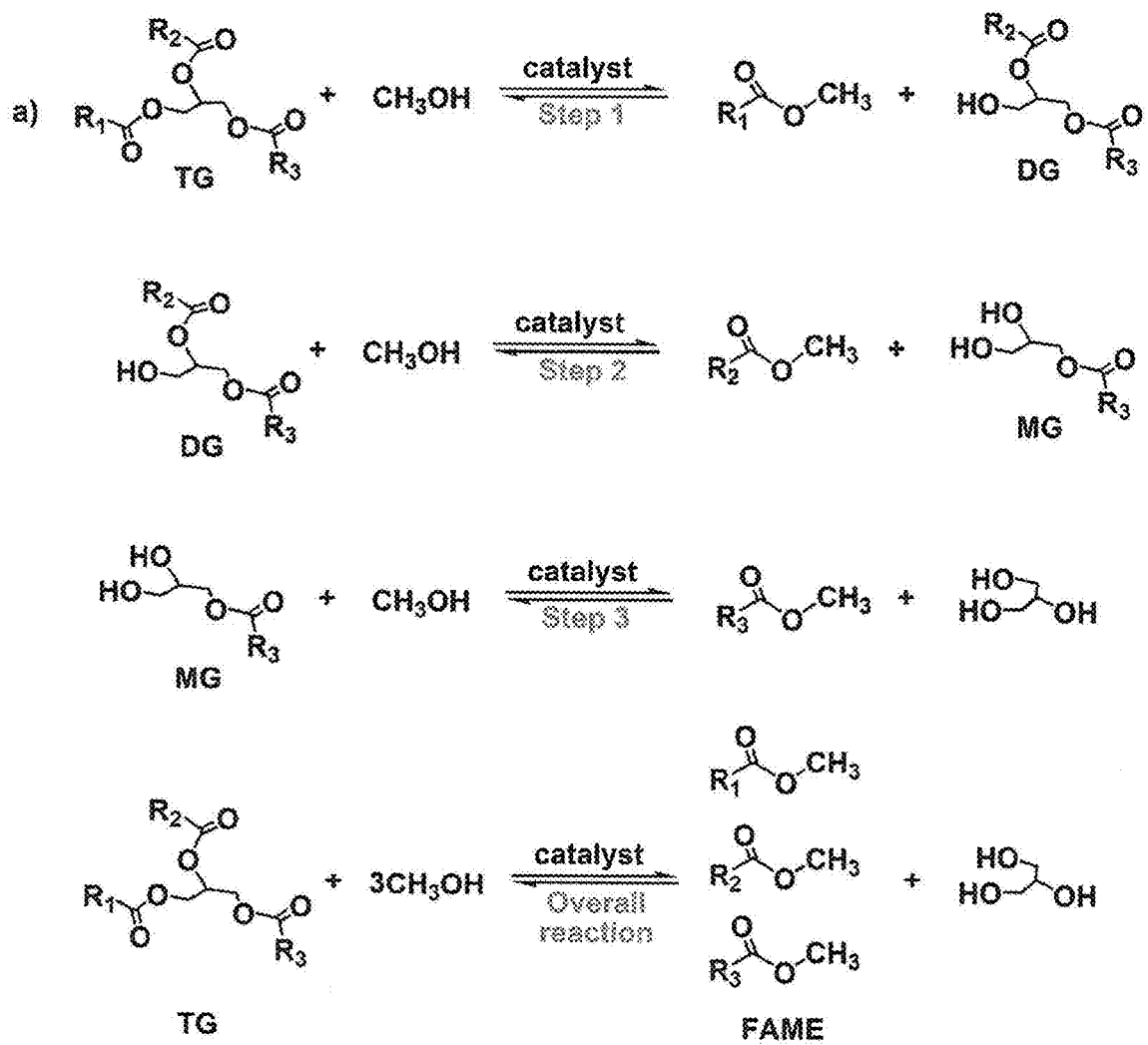
Figure 2:
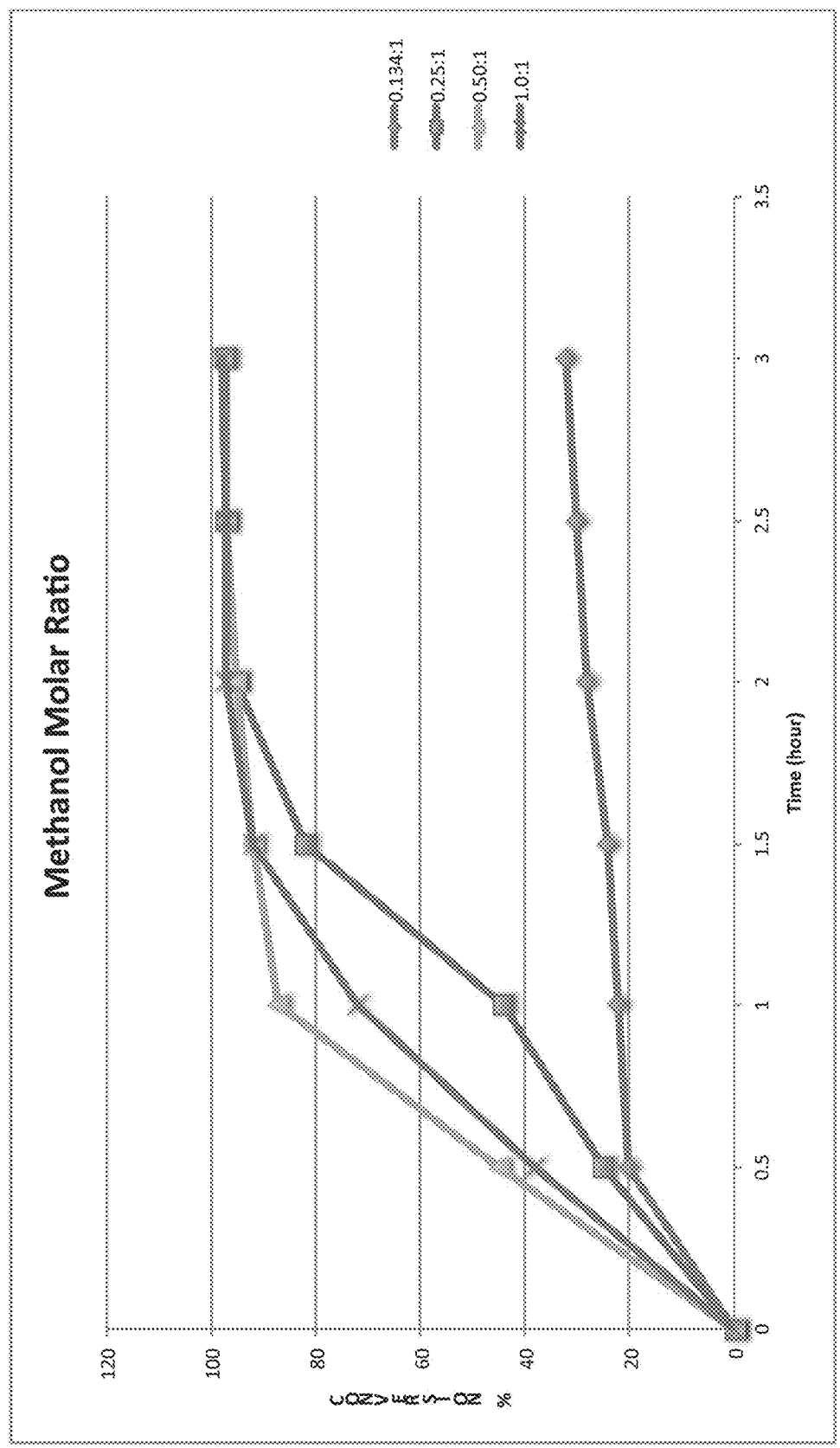
FIG. 2 is a line graph comparing reaction conversion at different methanol molar ratios at 1 weight % of UMAKAT in an illustrative embodiment.
Figure 3:
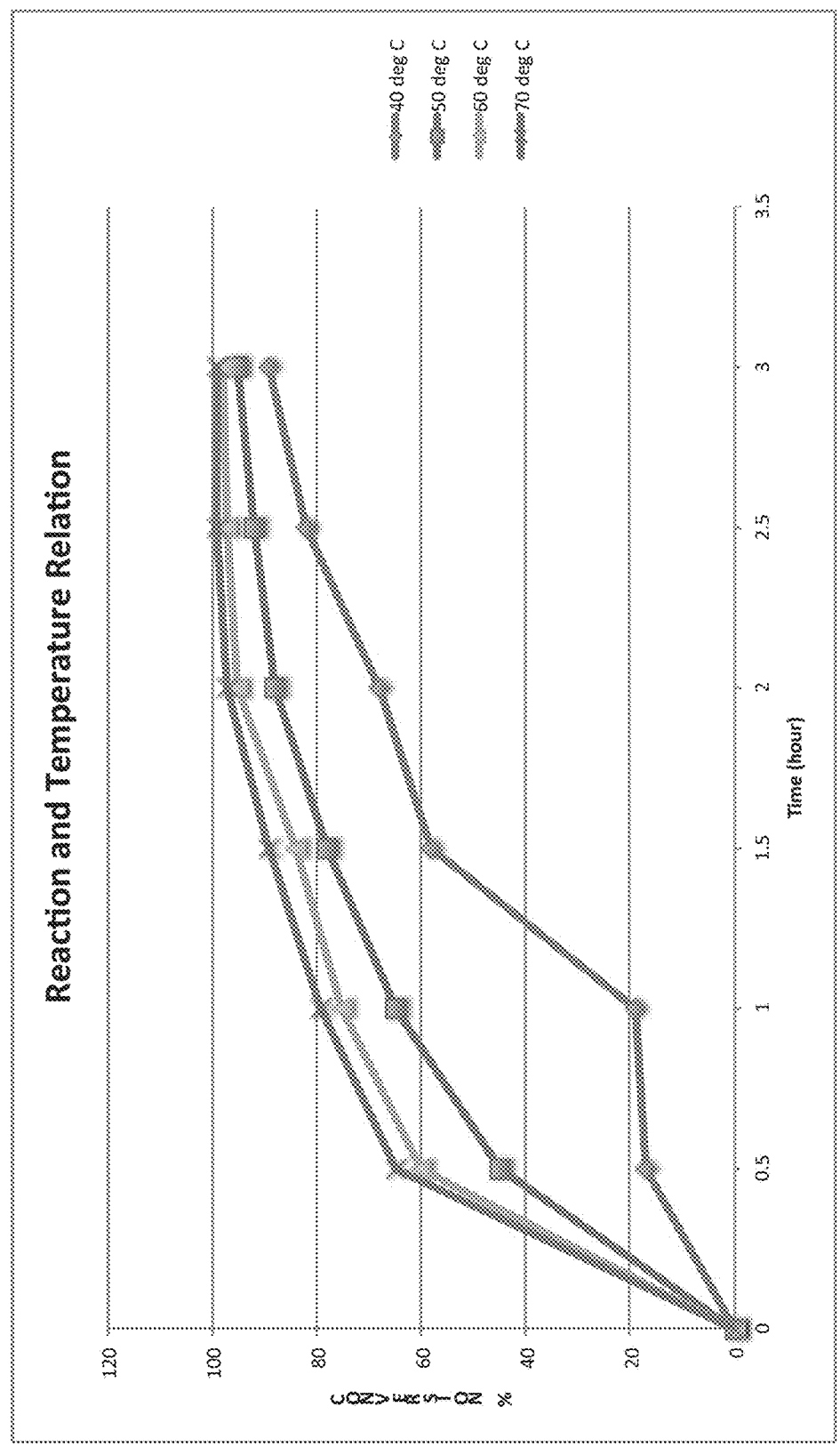
FIG. 3 is a line graph comparing reaction conversion at different temperatures at 1 weight % of UMAKAT in an illustrative embodiment.
Figure 4:
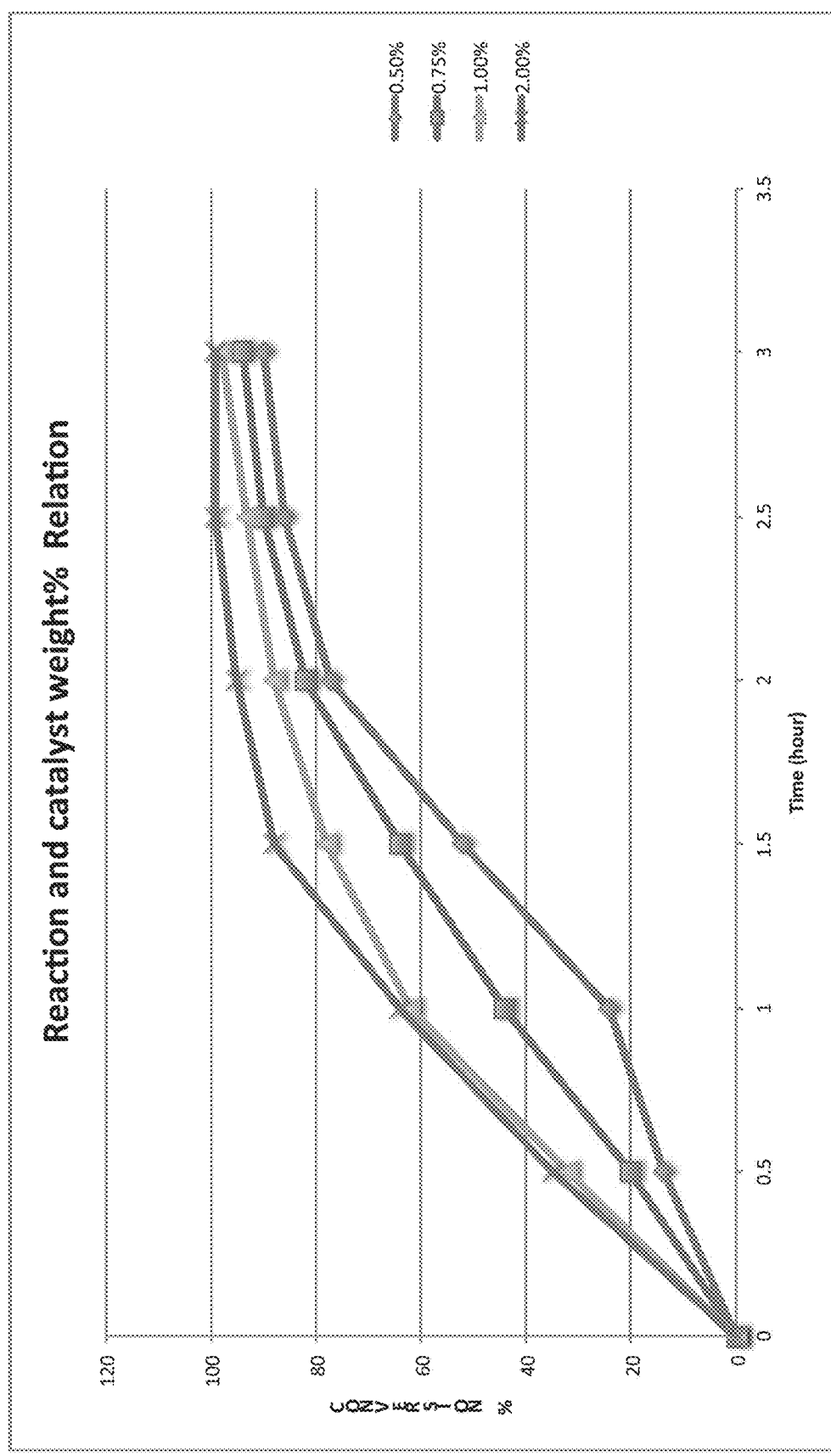
FIG. 4 is a line graph comparing reaction conversion at different UMAKAT weights at a fixed temperature of 60 degrees C. in an illustrative embodiment.
Figure 5:
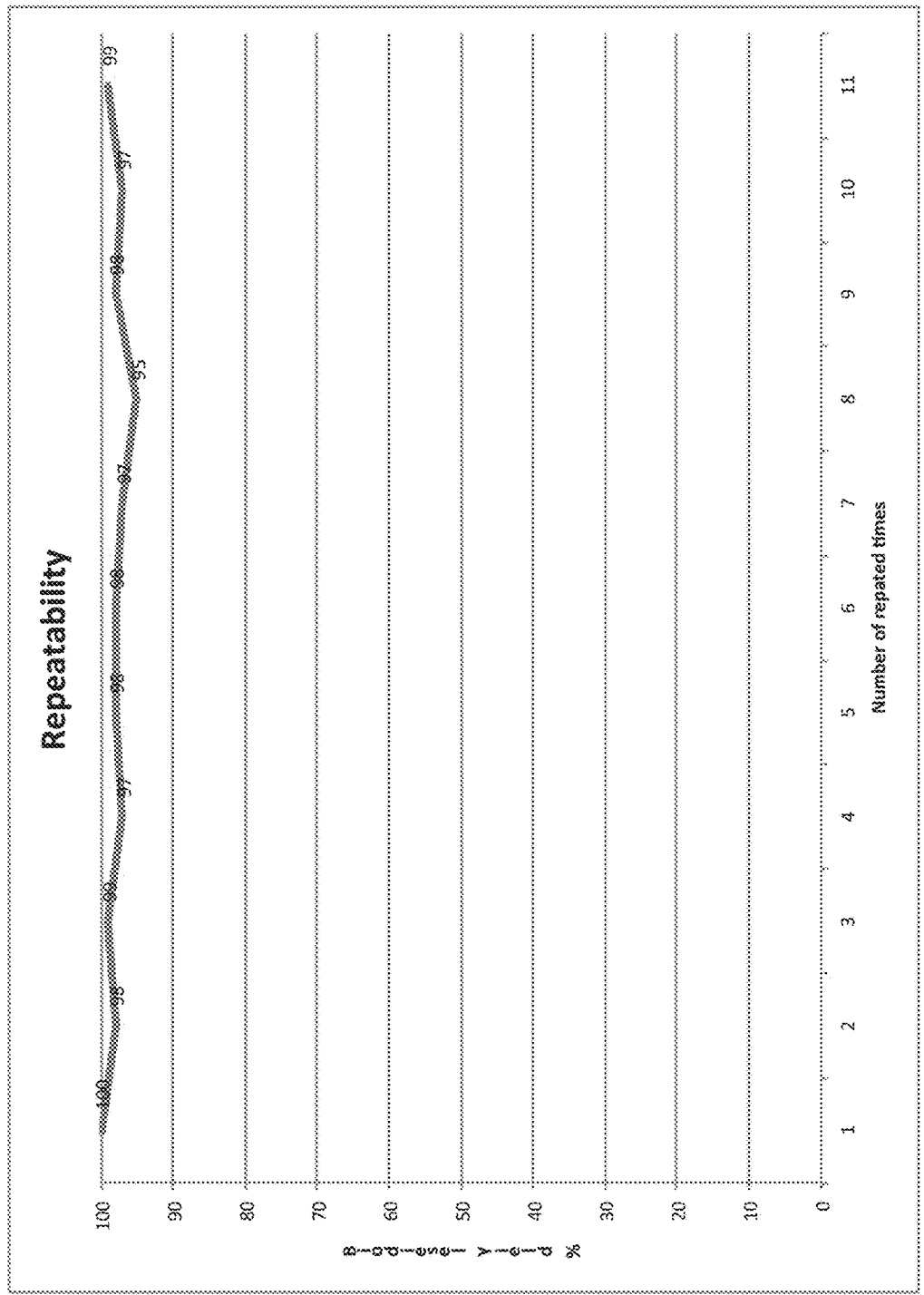
FIG. 5 is a line graph comparing biodiesel (i.e., alkyl ester) yield using the same UMAKAT for repeat trials in an illustrative embodiment.

The generic process for the transesterification reaction is shown in FIGS. 1A and 1B. FIG. 1A represents the overall transesterification reaction, while FIG. 1B represents not only the overall reaction but also the stepwise chemical reactions where the triglyceride (TG) ester is first converted to alkyl ester and diglyceride (DG) ester, then the DG ester is converted to alkyl ester and monoglyceride (MG) ester, and then the MG ester is converted to alkyl ester and glycerin.

In certain illustrative embodiments, UMAKAT can have a total surface area greater than 20 $m^2$/gm and an active surface area greater than 20 $m^2$/gm. As used herein, the term "total surface area" means surface area totally available, and the term "active surface area" means surface area available for reaction. The active surface area of UMAKAT is significant because the higher the active surface area, the greater the availability of active catalyst sites.

In certain illustrative embodiments, the heterogeneous compound can be porous. For example, UMAKAT can have an average pore diameter in the range from 1-10 nanometers (Nm). Pore diameter is measured by nitrogen adsorption. The pore diameter of UMAKAT is sufficient to allow migration or diffusion of reactant molecules into and out of the UMAKAT pores, in certain illustrative embodiments. This will determine the rate and extent of absorption of reactant molecules at the catalyst surfaces.

Other homogeneous transesterification processes call for the catalyst being dissolved in an alcohol, for example, methanol or ethanol, which needs to be removed post reaction. Further, the homogeneous catalyst is soluble in reactants and products, which requires steps to cleanse the alkyl ester and glycerin products. In contrast, in certain illustrative embodiments UMAKAT can form a slurry with triglyceride-containing oils and/or fats rather than alcohol for a better reaction conversion and easier separation of reactants and catalyst at the end of the reaction. In general, a catalyst slurry can be made with any oil/fat rather than methanol/ethanol solution (or any other alcohol) for CSTR type reactions. Further, in certain illustrative embodiments UMAKAT provides a uniform suspension throughout the reaction media. By comparison, a heterogeneous catalyst suspension in methanol/ethanol is not uniform and the catalyst particles settle at the bottom of the reactor vessel.

In certain illustrative embodiments, UMAKAT can be active at significantly less severe conditions than other heterogeneous catalyst systems. For example, other methanolysis transesterification heterogeneous catalysts require temperatures from 150 to 250 degrees C. and pressures of 300 to 400 psi. These operating conditions require that other processes using heterogeneous catalysts are carried out in fixed bed reactors.

In contrast, methanolysis transesterification using UMAKAT to manufacture biodiesel requires temperatures in the range from 40 to 70 degrees C. and atmospheric pressure conditions, in certain illustrative embodiments. Similarly, transesterification using UMAKAT to react, for example, dodecanol or other higher alcohols and triglycerides to manufacture biolubricants requires temperatures up to and slightly above 100 degrees C. and atmospheric pressure conditions, in certain illustrative embodiments. For these services, UMAKAT can be used in CSTR, fluidized bed and PFR reactor systems.

To ensure complete conversion of triglycerides, alcohol is added in excess of stoichiometric requirements, for instance 2 to 4 times that required to ensure the complete conversion of triglycerides to alkyl ester, in certain illustrative embodiments.

Furthermore, UMAKAT is an efficient catalyst in that it can be reusable. UMAKAT can also be used in existing transesterification process equipment without major revamping.

UMAKAT can be used for manufacturing ASTM D 6751 biodiesel and Technical Grade glycerin as well as biolubricants. Also, UMAKAT does not need water wash for post reaction treatment and does not require steps such as pH neutralization to cleanse products.

In order to facilitate a better understanding of the presently disclosed subject matter, the following examples of certain aspects of certain embodiments are given. In no way should the following examples be read to limit, or define, the scope of the presently disclosed subject matter.

Example 1

This example illustrates the preparation of a double metal salt catalyst with ceramic base support of zirconium oxide. In a typical catalyst preparation, a Group 1 metal hydroxide, in this Example potassium hydroxide, is mixed with a Group 2 metal hydroxide, in this Example calcium hydroxide, and dissolved in dilute phosphoric acid. This is then heated in a temperature range from 60 to 90 degrees C. As a result, a white precipitate is formed which is then washed with water and mixed with zirconium oxide powder. This material is calcined at 400-500 degrees C. for a minimum of 4 hours.

Example 2

This example describes the preparation of fatty acid methyl esters by transesterification of soybean oil with methanol using UMAKAT. In a typical reaction, commercial soybean oil (100 gms) and methanol (oil to methanol molar weight ratio of 1:6) and UMAKAT (2 to 6 wt % UMAKAT in oil) were charged to a 500 ml glass beaker and stirred at a speed of 300 to 500 rpm at a temperature of 60-80 degrees C. for about 10 to 30 minutes. It was then allowed to cool.

The UMAKAT was separated by filtration from the mixture of reaction products. The product mixture included unreacted methanol plus an upper layer of methyl ester and a lower layer of glycerin. Then, unreacted methanol was separated from each layer by distillation. The methyl ester was tested in a gas chromatograph.

The methyl ester analysis report is summarized in Table 1 below along with the ASTM spec for biodiesel.

TABLE 1

|  | UMAKAT | ASTM SPEC |
|---|---|---|
| Water & Sediment | 0.000 | .05 max |
| Cetane Number | 47.8 | 47 min |
| Cold Soak Filtration | 90 seconds for 300 ml | 300 sec max |
| Free glycerin | 0.005% | .02 max |
| Total glycerin | 0.191% | .24 max |
| Calcium, ppm | <1 | — |
| Magnesium, ppm | <1 | — |
| Sodium, ppm | <1 | — |
| Potassium, ppm | <2 | — |

Table 1 generally shows: no water and sediments are present in the alkyl ester product, only trace amounts of metals solids are present, and, as measured by the amount of glycerin in the product, the reaction is essentially complete conversion to methyl ester. The biodiesel made with UMAKAT was also assessed via the Cold Soak Filtration Test. In this test, a biodiesel liquid sample is chilled to below 32 degrees F. for 16 hours, restored to room temperature and passed thru a 0.5 micron filter. This ASTM test is passed if the filtration is complete within 300 seconds. The UMAKAT biodiesel passed thru the filter in 90 seconds.

Different oils and fats were tested for oil conversion to methyl ester using UMAKAT and the results are tabulated in the following table:

TABLE 2

| Test No. | Oil/Fat | Alcohol | % Oil conversion | Notes |
|---|---|---|---|---|
| 2 | Canola Oil | Methanol | 97.7 | — |
| 3 | Yellow grease | Methanol | 96.8 | — |
| 4 | Coconut Oil | Methanol | 98.2 | — |
| 5 | Cottonseed Oil | Methanol | 97.5 | — |
| 6 | Chicken Fat | Methanol | 97.2 | High Free Fatty Acid ("FFA") Oil first esterified with acid catalyst |

Table 2 shows that UMAKAT is effective for a wide variety of oils and fats.

FIGS. 2 thru 5 are heterogeneous catalytic kinetics graphs showing how the reaction proceeds at different temperatures, methanol ratios, and catalyst weight concentrations.

In certain illustrative embodiments, UMAKAT can be easily separated from reactants and products and reused, no leaching of metal ions into the reactant mixture was observed, and UMAKAT processing temperature and pressure are at moderate conditions which are significantly less severe than other heterogeneous catalytic transesterification processes.

Additionally, in certain illustrative embodiments UMAKAT can be used to process low cost/unrefined oils and/or fats containing impurities that, for example, cause discoloration of the feedstock. Further, post reaction process waste is reduced as neutralization and water wash of products are not required. Relative to other catalysts and processes, UMAKAT is highly active at comparatively low temperature and pressure. Also, UMAKAT produces much fewer impurities in the alkyl ester and glycerin products and thus the products are much cleaner at the end of the reaction. Further, no pH neutralization water wash is required and salts from glycerin neutralization do not end up in the alcohol distillation column. Finally, UMAKAT transesterification facilities are comparatively lower in cost to install, maintain and operate.

As used herein, the term "in the range from" and like terms is inclusive of the values at the high and low end of said ranges, as well as reasonable equivalents.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter.

Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the appended claims.

What is claimed is:

1. A method of preparing a transesterification catalyst comprising:
   mixing a metal hydroxide with the metal selected from the group consisting of potassium, sodium and lithium with a metal hydroxide with the metal selected from the group consisting of calcium, magnesium, and barium in a ratio of about 1:10 by weight to form a component mixture;

dissolving the component mixture in phosphoric acid;

heating the component mixture to a temperature in the range from 60-90 degrees C.;

precipitating a solid compound;

mixing the precipitate with ceramic substrate in a ratio of about 2:10 by weight and washing with water to form a precipitate/ceramic substrate mixture; and calcining the precipitate/ceramic substrate mixture at a temperature in the range from 400-500 degrees C.

2. The method of claim 1, wherein the precipitate/ceramic substrate mixture is calcined by heating for four hours or greater.

* * * * *